US011433319B1

(12) United States Patent
Eickhoff et al.

(10) Patent No.: US 11,433,319 B1
(45) Date of Patent: Sep. 6, 2022

(54) SYSTEMS AND METHODS FOR ORGANIC ISOLATION OF TARGET COMPOUNDS FROM SOURCE MATERIALS

(71) Applicant: Rocky Mountain Extraction Services, LLC, Windsor, CO (US)

(72) Inventors: John Eickhoff, Windsor, CO (US); Jerry Van Sickle, Loveland, CO (US); Scott McWhorter, Windsor, CO (US)

(73) Assignee: Rocky Mountain Extraction Services, LLC, Windsor, CO (US)

( * ) Notice: Subject to any disclaimer, the term of this patent is extended or adjusted under 35 U.S.C. 154(b) by 0 days.

(21) Appl. No.: 17/671,189

(22) Filed: Feb. 14, 2022

Related U.S. Application Data (60) Provisional application No. 63/149,148, filed on Feb. 12, 2021.

(51) Int. Cl.
| | |
|---|---|
| *C07C 39/04* | (2006.01) |
| *B01D 11/00* | (2006.01) |
| *B01D 9/00* | (2006.01) |
| *B01D 11/02* | (2006.01) |

(52) U.S. Cl.
CPC ........ *B01D 11/0288* (2013.01); *B01D 9/0045* (2013.01); *B01D 11/0203* (2013.01); *B01D 11/0284* (2013.01); *B01D 11/0292* (2013.01); *C07C 39/04* (2013.01)

(58) Field of Classification Search
CPC .... C07C 39/04; B01D 11/0288; B01D 9/0045
See application file for complete search history.

(56) References Cited

U.S. PATENT DOCUMENTS

| | | | |
|---|---|---|---|
| 9,765,000 | B2 | 9/2017 | Nadal Roura |
| 9,815,810 | B1 | 11/2017 | Ogilvie et al. |
| 10,189,762 | B1 | 1/2019 | Oroskar et al. |
| 10,745,644 | B1 | 8/2020 | Ellis et al. |
| 10,751,640 | B1 | 8/2020 | Ferraro et al. |
| 10,858,303 | B1 | 12/2020 | Ferraro et al. |
| 10,967,018 | B2 | 4/2021 | Robertson |
| 11,148,988 | B2 | 10/2021 | Opperman |
| 2020/0361841 | A1 | 11/2020 | Stone et al. |

FOREIGN PATENT DOCUMENTS

EP    3274321 B1    9/2019

OTHER PUBLICATIONS

Organic Production & Handling Standards | Agricultural Marketing Service; United States Department of Agriculture Agricultural Marketing Service, accessed Feb. 7, 2022. 1 page.
U.S. Appl. No. 63/149,148, filed Feb. 12, 2021, first named inventor: Eickhoff.

*Primary Examiner* — Sikarl A Witherspoon
(74) *Attorney, Agent, or Firm* — Santangelo Law Offices, P.C.

(57) ABSTRACT

Embodiments may provide systems and method for purifying natural and/or organically certified nutraceuticals, such as cannabinoids. Embodiments may include refined or unrefined solvents, refined or unrefined plant extracts, refined or unrefined source compounds to be purified to any degree. Embodiments may reduce the concentration of impurities such as other cannabinoids (e.g., THC), terpenes, pesticides, herbicides, mycotoxins, heavy metals, other solvents (e.g., ethanol), waxes, or other impurities. Embodiments may increase the concentration of target compound(s) from its respective source material.

56 Claims, 3 Drawing Sheets

SYSTEMS AND METHODS FOR ORGANIC ISOLATION OF TARGET COMPOUNDS FROM SOURCE MATERIALS

This is a U.S. non-provisional patent application claiming priority to and the benefit of U.S. provisional patent application No. 63/149,148 filed Feb. 12, 2021, hereby incorporated by reference herein in its entirety.

BACKGROUND OF THE INVENTION

It is desirable to develop effective methods for the extraction and isolation of materials perhaps resulting in organic products. Natural products may be used as natural medicines providing medicinal benefits. Extraction may be used to separate a desired product form a raw material. This may include solvent extraction, distillation method, pressing and sublimation, or the like. Organic is a labeling term that indicates that a food or other agricultural product has been produced through approved methods. These methods integrate cultural, biological, and mechanical practices that foster cycling of resources, promote ecological balance, and conserve biodiversity. Synthetic fertilizers, sewage sludge, irradiation, and genetic engineering may not be used for a product to be labeled as "organic."

A general method of crystallization has been used as a purification technique for centuries. Conventionally, general steps to crystallize solid compound(s) may start with a crude mixture containing target compound(s) dissolved in a solvent. Then the solubilizing properties of the solvent may be reduced by lowing its temperature, removing the solvent via vaporization, and/or adding an anti-solvent, which may allow crystals to form in the solution. These crystals may then be filtered and rinsed with an appropriate solvent and dried. This general method may be used for crystallizing cannabinoids but may uses petroleum-based hydrocarbon solvents (e.g., butane, pentane and heptane). Though, these techniques create very pure products, the use of the petroleum-based solvents deem these products unlikely candidates for getting organically certified by United States Department of Agriculture ("USDA") and international certifying agencies. With such solvents, there is an inherent danger for the manufacturers to inhale and even ignite the volatile solvents. It is also very difficult to completely remove all the petroleum-based solvents from isolated solids, where these residual solvents may eventually be ingested and/or applied topically to the end consumer.

As such, there is a need for USDA and internationally certifiable products which can be used to purify compounds that can be safer for the manufactures and consumers.

SUMMARY OF THE INVENTION

This application includes a variety of aspects, which may be selected in different combinations based upon the particular application or needs to be addressed.

It is an object to provide organic isolation of target compounds from crude source materials.

Another object is to provide non-ethanol plant-based solvents in purifying compounds.

It is yet another object to provide organic isolated cannabidiol using a non-ethanol plant-based solvent.

Another object is to provide an organic isolated cannabidiol with a high purity.

Naturally, further objects, goals and embodiments of the inventions are disclosed throughout other areas of the specification, claims, and drawings.

DETAILED DESCRIPTION OF THE INVENTIONS

It should be understood that embodiments include a variety of aspects, which may be combined in different ways. The following descriptions are provided to list elements and describe some of the embodiments of the application. These elements are listed with initial embodiments; however, it should be understood that they may be combined in any manner and in any number to create additional embodiments. The variously described examples and preferred embodiments should not be construed to limit the embodiments of the application to only the explicitly described systems, techniques, and applications. The specific embodiment or embodiments shown are examples only. The specification should be understood and is intended as supporting broad claims as well as each embodiment, and even claims where other embodiments may be excluded. Importantly, disclosure of merely exemplary embodiments is not meant to limit the breadth of other more encompassing claims that may be made where such may be only one of several methods or embodiments which could be employed in a broader claim or the like. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Embodiments may provide methods and systems for isolating compounds including but not limited to: a method for isolating compounds comprising the steps of providing a crude source material having a target compound and at least one non-target compound; adding a non-ethanol plant-based solvent to said crude source material; mixing said crude source material with said non-ethanol plant-based solvent to form a solution; forming crystals comprising said target compound from said solution; separating said crystals comprising said target compound from said solution; and perhaps even yielding organic crystals of said target compound from said crude source material.

Embodiments may also include a system to isolate compounds comprising: a vessel configured to contain a crude source material having a target compound and at least one non-target compound; a non-ethanol plant-based solvent configured to be added to said crude source material in said vessel; a mixer configured to mix said crude source material with said non-ethanol plant-based solvent to form a solution; a crystal separator configured to separate crystals comprising said target compound from said solution; and perhaps even a collection of organic crystals of said target compound isolated from said crude source material.

Embodiments may provide crystallization of a crude source material to produce purified desired solids in a way that can be certifiably organic, presuming all crude mixtures are certified organic and/or allowed as processing aids in organic certification. The purifying materials may not use petroleum-based solvents, and therefore can allow for USDA and even internationally certified organic products. Specifically, processes may use natural and/or USDA Certified Organic plant-based solvents including, but not limited to, plant-based solvents, non-ethanol plant-based solvents, terpenoid blends, terpenoid isolates, essential oils, nut oils, or the like to crystallize desired compound(s) and even remove undesired constituents in a complex mixture.

Figure 1:
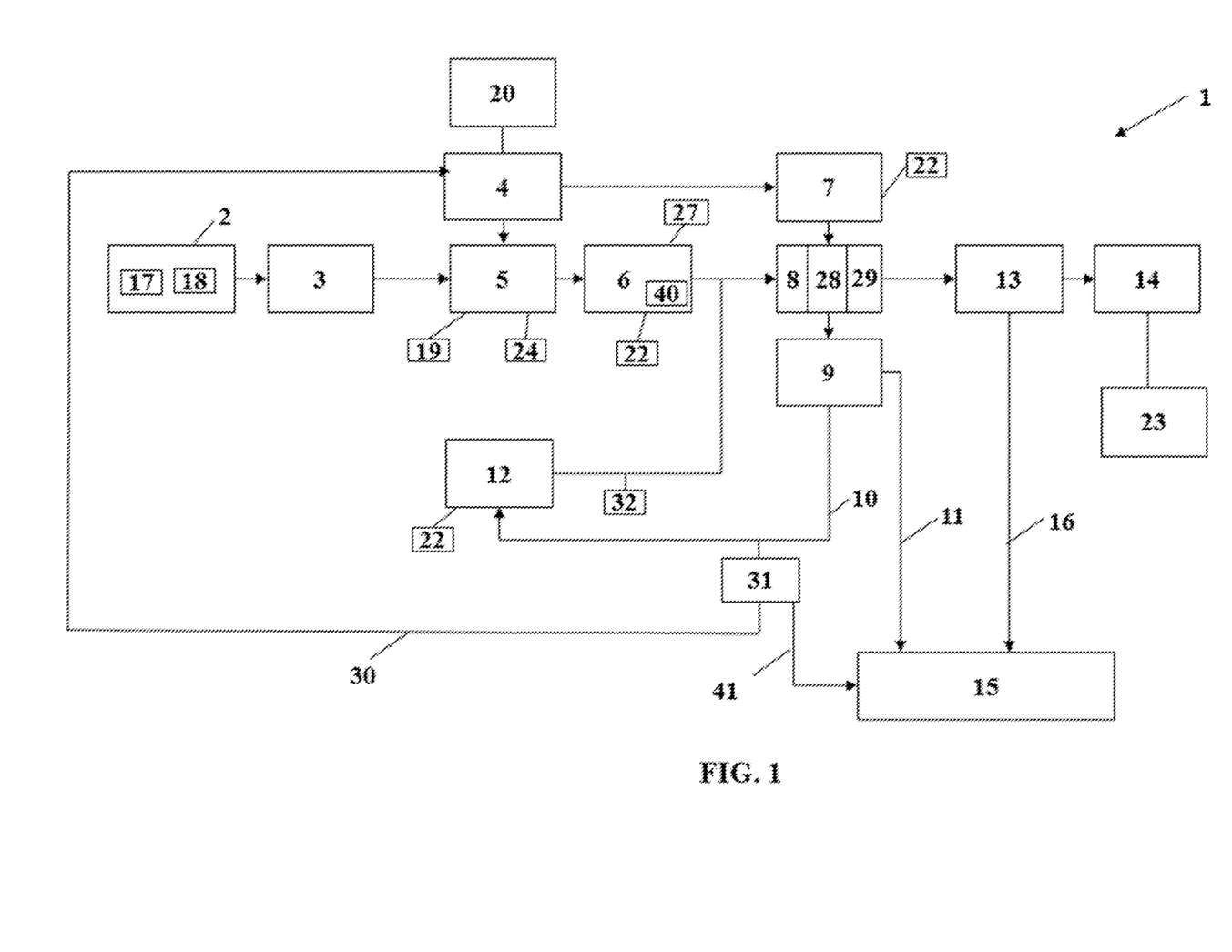
FIG. 1 shows a non-limiting example of a flow diagram of a system that can be used to isolate compounds in accordance with some embodiments.

As may be understood in FIG. 1, a crude source material (2) may contain a target compound (17) and at least one non-target compound (18). A crude source material may be any material and may include oil extracted from *Cannabis sativa*, oil extracted from USDA certified organic high-cannabidiol *Cannabis sativa*, or the like. A target compound which may be at least one target compound may be isolated from a crude source material and may include, but is not limited to, cannabinoids, cannabidiol (CBD), cannabigerol (CBG), cannabinol (CBN), cannabidiolic acid (CBDA), cannabigerolic acid (CBGA), cannabichromene (CBC), cannabidivarin (CBDv), cannabinoids excluding tetrahydrocannabinol (THC), vitamins, nutraceuticals, supplements, pharmaceuticals, phtyochemicals, any combination thereof, or the like. A non-target compound (18) or at least one non-target compound may include, but are not limited to locally, regionally, federally and even internationally regulated compounds, impurity, solvents, residual solvents, ethanol, terpenes, waxes, cannabinoids, tetrahydrocannabinol, tetrahydrocannabinolic acid, mycotoxins, herbicides, pesticides, heavy metals, agrochemicals, phytochemicals, lipids, and any combination thereof, or the like. Non-target compounds may be removed from a starting crude source material. Once removed via a system (1), these compounds can be disposed of, destroyed, further processed, or the like perhaps following local, state, federal, or international laws after removal.

Embodiments of the application may be applied to a variety of products. It may be important to understand a crude source material before designing a purification process. In the case of cannabinoids, a crude source material may be greater than about 40% concentration of total cannabinoids perhaps with a variety of qualities. A concentrate (3) such as a source oil may be extracted with water, ethanol, carbon dioxide, may be heat-pressed, may be a plant-based oil, or the like. A source oil may be winterized or not, may be distilled or not, may be organic or not, may be a product from or even a side-product from a purification process, or the like. For simplicity's sake, the descriptions of some embodiments may primarily discuss oil that may have been extracted from USDA certified organic high-cannabidiol hemp with carbon dioxide, distilled, and even unwinterized in a non-limiting fashion. Of course, any crude source material, oil, extract, or the like may be used and all are included in the scope of this application.

There are a variety of options for the processing steps to purify and isolate a compound from a source material which may depend on application, process capabilities, a desired final product, or the like. The process steps described herein are non-limiting examples and the order of process flow and each variation may be changed or varied as needed.

In various embodiments, a crude source material containing target compound(s) may be dissolved into a solvent, perhaps using crystallization methods. A solvent, such as a non-ethanol plant-based solvent (4) may be configured to be added or even added to a crude source material (2). A solvent may include plant-based solvents. In some embodiments, a solvent may be a non-ethanol plant-based solvent (4) which may include but is not limited to essential oils, terpenes, terpenoids, nut oils, cooling oils, fermented alcohols, each blended, isolates, refined, or unrefined, and combination thereof, or the like. Solvents may be natural, organic, non-organic or otherwise. A non-ethanol plant-based solvent may not contain ethanol. In some embodiments, a plant-based solvent may be orange essential oil. It may be an organic, cold pressed, then distilled orange essential oil ("OEO"). Of course, any plant-based solvent may be used and all are included in the scope of this application. In some embodiments, a solvent may be pre-processed (20) perhaps to remove at least one impurity such as undesired colors, or the like.

Figure 2:
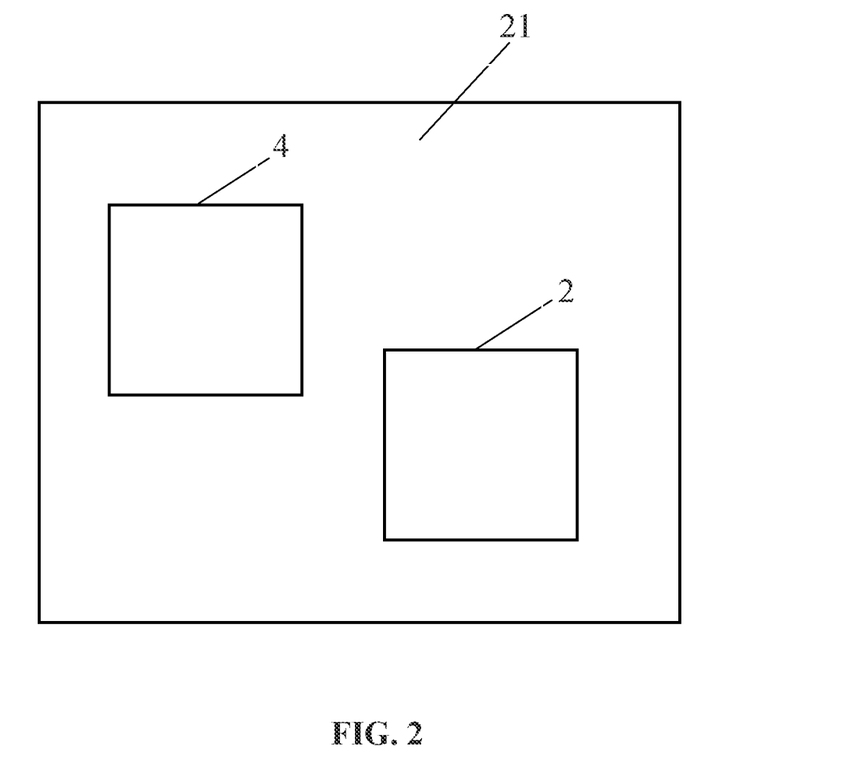
FIG. 2 shows a non-limiting example of a vessel in accordance with some embodiments.

As understood from FIG. 1, a crude source material may be mixed with a non-ethanol plant-based solvent to form a solution (5) perhaps with a mixer (19). Mixing may include stirring, mechanical mixing, or the like. A crude source material may be warmed to about 20° C. or more. A crude source material may be added to a vessel (21) configured to contain the crude source material as may be understood from FIG. 2. One vessel or more than one vessel may be used between the steps of mixing, dissolving, crystallizing, and even filtering desired components. A vessel (21) may be a temperature-controlled vessel, a stainless-steel vessel, a jacketed vessel, a high-density polyethylene vessel, a food grade plastic vessel, a glass vessel, and any combination thereof, or the like. A vessel may be made of a material so that a plant-based solvent may not dissolve the material. A vessel may not include a Nutsche filter dryer in some embodiments. In others multiple vessels including a Nutsche filter dryer may be used. In some embodiments, a crude source material may be added to a warm vessel that may be greater than about 20° C. Embodiments may provide warming the crude source material to a temperature greater than about 40° C.

Warm, liquified crude source material or a concentration thereof may be added to a vessel perhaps keeping the temperature warm enough to stir and cool enough to avoid volatilizing the plant-base solvent. In the case of OEO, a flash point for a major component, limonene is approximately 45° C. A plant-based solvent, such as OEO, may be added to the crude oil slowly at room temperature or even an elevated temperature, and even blended until a solution (7) is a homogenized solution. A non-ethanol plant-based solvent may be warmed when it is added to a warm crude source material. A solution may be warmed while mixing perhaps with a mixer (19) of the crude source material with a non-ethanol plant-based solvent. A solution (7) may be filtered (24) to ensure all small particles may be removed before a crystallization process.

Embodiments of the application may provide a ratio between a crude source material and a solvent, which can range from about 2% to about 75% OEO in the crude oil. For example a ratio of non-ethanol plant-based solvent to crude source material may be between about 2% non-ethanol plant-based solvent to about 98% crude source material to about 75% non-ethanol plant-based solvent to about 25% crude source material. In the case of cannabidiol ("CBD") or any other compound that can be readily tested for concentration, a ratio may be determined by the calculated concentration post blending. For example, if 20 kg of crude oil has a concentration of about 77% CBD and the target concentration is 64% CBD for starting the crystallization process, approximately 4 kg of OEO could be added. This concentration may change perhaps based on the temperature of the crystallization event. In this non-limiting example, the crystallization may occur at about 20° C. As the target crystallization temperature may get lower, the target concentration of CBD may also get lower, for example, the crude oil may be diluted with OEO to about 52% CBD so it may crystallize at about 2° C.

Figure 3:
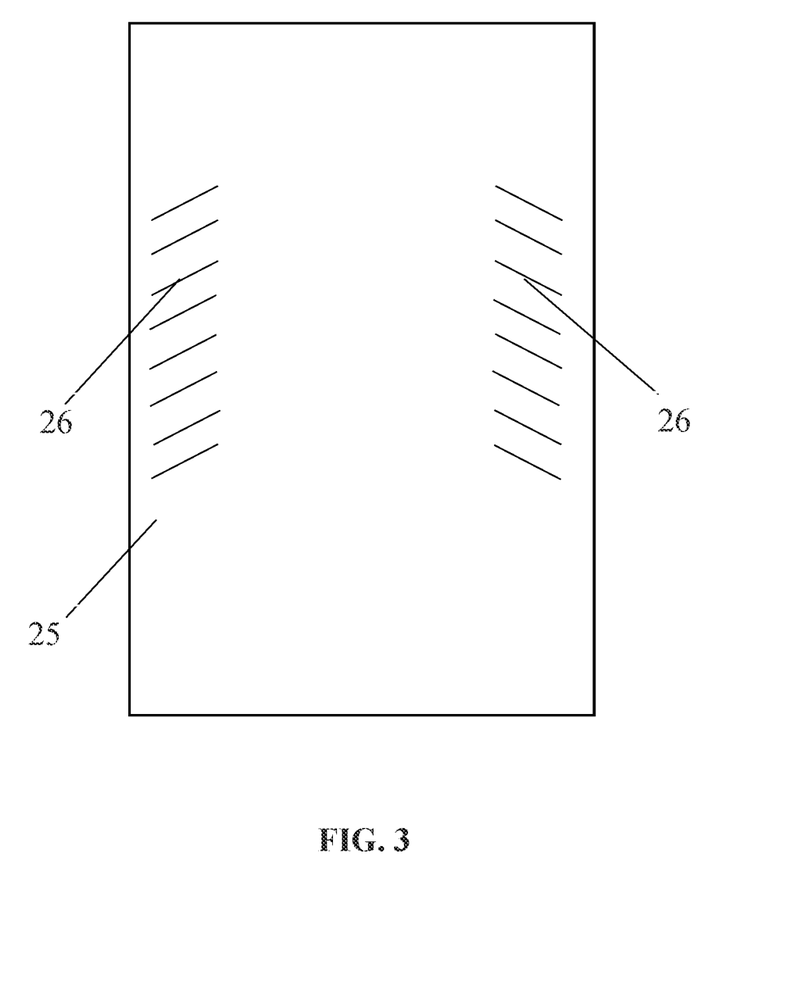
FIG. 3 shows a non-limiting example of a container in accordance with some embodiments.

Crystals (40) of a target compound may be formed (6) from a solution. Once a solution may be homogenized, it may be helpful to slowly cool the solution to a target temperature perhaps with a cooler (22). A temperature may be around 20° C., between about 20° C. and about 2° C., or the like. Inducing crystallization and nucleation may be attempted by adding a single crystal of a target compound to a solution, adding up to about 10% of total mass of a target compound or any other compounds to a solution, gently stirring a solution, providing a container (25) with a rough surface (26) as may be understood from FIG. 3 where the target compound(s) may nucleate on the surfaces, or perhaps even allowing the nucleation to occur spontaneously, or the like.

In some embodiments, a solution may be gently stirred or even left still during a crystal formation step. Strict temperature control of a crystallizing chamber may be helpful in getting consistent and predictable results; this may be done by using a jacketed vessel that can continuously temperature-controlled medium through the vessel's jacket or even using an appropriately sized fridge/freezer/oven/temperature-controlled room, or the like.

It may be desirable to determine if crystallization is complete before separating crystals from a solution. If analytical equipment may be available, monitoring a concentration of a solution, residual composite, mother liquor, or the like may help as an indicator for when the crystallization may be complete. When a CBD concentration lowers to or even approaches a saturation concentration, the crystallization could be complete. If analytical equipment is not available, determining completeness may be based on time and/or appearance, or the like. In some embodiments determining when crystallization is complete may include but is not limited to monitoring (27) a solution such as monitoring a temperature of a solution; monitoring a target compound concentration in a solution; monitoring an amount of time a solution has been cooled; monitoring an appearance of a solution; any combination thereof; and the like.

Crystals (40) may be separated from a solution perhaps with a crystal separator (8) configured to separate crystals comprising a target compound from a solution as may be understood in FIG. 1. A crystal separator (8) may include a filter, vacuum filter, pressure filter, pressure filter with gas, pressure filter with nitrogen gas, or the like which may provide filtering crystals from a solution, vacuum filtering crystals from a solution, pressure filtering crystals with gas from a solution, pressure filtering crystals with nitrogen gas from a solution, or the like.

Crystals may be filtered and even washed perhaps with a cold and/or saturated washing solution. The washing may even remove residual plant-based solvent via a variety of methods described herein. In embodiments, a saturated solution may be used which can be effective in minimizing loss of target compounds. Solvent removal methods may include but is not limited to high pressure gas, liquid, supercritical fluid, distillation, vacuum filtration, or the like.

There may be several techniques and pieces of equipment that can be used to filter a liquid with solids ("slurry"). After crystals are separated from a solution a residual composite (9) containing a remaining part of a solution may be collected. For filtration, vacuum filtration may be possible and even likely for entry-level, economic filtration, and can range in scale between about 10 g to about tens of kg. To filter, pour a mixed slurry into a filtration funnel as the vacuum may be pulling liquid such as a residual composite through the filter, perhaps leaving the solids such as crystals on the filter. Crystals may be organic crystals (14) and even a collection of organic crystals (14) of a target compound yielded from a crude source material. Crystals may be broken up perhaps with a crystal breaker (23). In some embodiments organic crystals may be yielded from a crude source material without using a centrifuge in the process.

Filtration centrifuges may be another option for filtering a slurry. A slurry may be placed in a centrifuge and started filtering the slurry in batches or a slurry may be poured into a continuous feed process until filtration may be complete.

A residual composite (9) which may be a filtrate of a filtration or a remaining part of a solution after crystals are separated may be collected and even resubmitted for the crystallization at a lower temperature than the first pass of purification. For example, if the first crystallization was done at about 20° C., the second crystallization may be done at about 0° C. In embodiments, a residual composite may be processed (10) by cooling perhaps with a cooler (22) at a lower temperature than a temperature of a previous solution and supplementary crystals (12) comprising a target compound from a residual composite may be formed and collected.

Non-ethanol plant-based solvent (31) may be separated from a residual composite and may be reused (30) in a process or method such as to mix with a crude source material, used in a wash solution, or the like. Any waste (11), (41) from such separation or from a residual composite may be non-target waste (15) and may be disposed. A target compound (32) may be separated from a residual composite.

In embodiments, a crude source material may be processed so that a concentration of at least one non-target compound may be decreased.

A wash (28) may be performed to the solids such as crystals after being separated from a solution. Washing perhaps with a wash solution (7) may ensure that a residual plant-based solvent and any of its contents (e.g., potential impurities) are removed, though it may not be necessarily needed depending on desired end-product. A wash solution (7) may include but is not limited to residual composite, a crystallizing solvent, a non-ethanol plant-based solvent, a different non-ethanol plant-based solvent than used with a mixing step, a solvent mixed with a target compound, a solvent mixed with a crude source material, any combination thereof, or the like. A wash solution may be cooled perhaps with a cooler (22) before using to wash crystals perhaps to between about −40° C. and about 40° C. Though any temperature may be used. Wash solution may be reused in a method as may be understood in FIG. 1.

A washing solution can be made from a plant-based solvent blended with the compound(s) that is being purified. This may allow for less dissolving of the target compound(s) in the washing liquid. In the case of CBD crystallization with the goal of washing away residual THC, OEO can dissolve distillate having high concentrate of CBD and non-detect levels of THC to reach its saturation point (roughly 29% CBD) at about −20° C. Similarly, a mixture of OEO and CBG with non-detect levels of THC can be used as a washing solution to a similar end with possible residual CBG left with the solids. In some embodiments, organic crystals of a target compound can include organic cannabidiol having a purity of greater than about 95%.

After the batch of CBD crystals may be filtered, either the very cold plant-based solvent or even a saturated solvent may be used to wash the crystals at about −20° C. perhaps while using vacuum, pressured gas, centrifugal forces, or the like to remove most of the solvent.

In some embodiments, crystals may be rewashed perhaps several times with a wash solution. After washing, the wash solution may be removed from the crystals (29). There may be several options for removing any residual wash solvent, perhaps depending on the crystallization system (e.g., the target compounds used, solvents used, etc.). This may include but is not limited to removing wash solution from crystals with high pressure gas; removing wash solution from crystals with liquid; removing wash solution from crystals with a supercritical fluid; removing wash solution from crystals with distillation; removing wash solution from crystals with vacuum filtration; removing wash solution from crystals with vacuum filtration while using a blanket of inert gas during said filtration; adding heat to crystals; adding heat to crystals while pulling a deep vacuum; heating crystals in a vacuum oven; processing crystals in a distillation apparatus; or the like.

Vacuum filtration may be used as a continuation of a filtration perhaps by extending the time of filtering the solid and/or the negative pressure applied to the filtered crystals. Using a blanket of relatively inert gas such as nitrogen, argon or carbon dioxide, or the like in a filter may help preserve the quality of the final product. This method of removing a wash solvent can take an extended period of time and/or may provide incomplete solvent removal depending on the desired final product.

High pressure gas/liquid/supercritical fluid (e.g., nitrogen, carbon dioxide, water and/or argon, or the like) may be used to remove the wash solvent. This method of wash solvent removal may require an extended period of time depending on the desired final product. High-pressure fluids/liquids (e.g., super- or even subcritical carbon dioxide), may require strict temperature and pressure control, as the fluid may dissolve much of the target compound(s). The two temperature/pressure regions of carbon dioxide may be in the cold and low pressure (e.g., <about 10° C., about 800 to about 2000 PSI), and in the low density, supercritical region (e.g., >about 35° C., about 900 to about 1200 PSI). Properties, such as melting point and solubility may be considered when attempting this removal method.

Distillation can be used to remove more volatile compounds. In the cases of using essential oils and/or terpenes, these more volatile compounds can be removed using lower temperatures and pressures. On the other hand, if nut or cooking oils may be used for the crystallization and/or washing, the target compound(s) may be more volatile, and thereby being distilled first. As can be imagined, solid crystals may be melted in this process and resolidified as an amorphous solid.

Clarifying (13) of crystals can be used to remove residual color and even odorous compounds perhaps by passing crystals or oil through or even mixing with activated charcoal, bentonite clay, silica gel, or the like. Likewise, solid crystals may be melted in this process and resolidified as an amorphous solid. Any waste (16) from a clarification process may be may be non-target waste (15) and may be disposed.

A crusher (23) such as a pulverizer, grinder, mill, or the like may be options for re-making the melted product or even processing crystals into a free-flowing powder, if that is the desired state.

Embodiments may utilize cannabinoid isolation, organic solid isolates, B vitamins, piperine, biotin, curcumin, pharmaceuticals, nutraceuticals, or the like. Embodiments may use all natural and/or USDA certified organic materials in order to purify crude or refined material perhaps to increase the concentration of target compound(s) and/or remove a portion or a total of the undesired impurities from the target compound(s) or the like. This may be a method of crystallization used in an unconventional way where the purified products never come in contact with a petroleum-based solvent.

Solvents may be recycled perhaps via distillation which may make a process more cost-effective. Solvents may be naturally occurring, perhaps easy to extract, and even commercially available plant-based liquids, which may yield organically certified products.

Embodiments may allow recycling of plant-based solvents and recovered dissolved target compound(s). Firstly, a solvent may be reused and even purified via distillation. The residual composite and wash solvent (if the same) may be combined and may be distilled (roughly 100° C., about 100 mTorr in the case of monoterpenes) from the mixture.

A consideration may need to take place with regards to the impurities that are intended to be removed. Analytical capabilities could be useful in tracking the impurities to determine what materials are safe to blend, purify, and/or use, or the like. If the impurities are volatile, they may distill with the solvent, which may deem the solvent not reusable. If the solvent has a high boiling point, it may be impractical to distill, so the impurities and/or reusable target compound(s) may be able to be distilled out of the solvent. If the target and impurity compounds co-distill, be aware that the impurities may be in a higher ratio to the target compounds as compared to original starting crude material of the crystallization process. If the re-concentrated target compound mixture may be viable for crystallization, some adjustments to the solvent/crude oil ratio may be made.

Stemming from the goal of efficiency, embodiments may provide using very little solvent and even reusing plant-based solvent post-purification. As one non-limiting example, compared to conventional petroleum-based crystallization of CBD, embodiments may provide use of about 4% of the total volume of the solvent that is used in U.S. Patent App. Pub. No. US 2020/0361841, hereby incorporated by reference herein, to produce high purity CBD. Using less solvent can help avoid wasting solvent and the processing equipment can be smaller while processing more of the target product, or the like. Reuse of a solvent can be achieved by combining a mother liquid and washing solvent, then distilling it to leave behind residual impurities from the crystallization process. The residue can then be disposed of, destroyed, further processed, and the like to meet local, state, federal, and international laws, (e.g., in the case of THC concentration).

A saturated solution may be used with a target or even surrogate compound(s) of a solvent, such as a plant-based solvent or non-ethanol plant-based solvent. This technique may help to lower the solubilizing power of the plant-based solvent to possibly lessen dissolving of the crystals as it washes the crystals' surfaces. Alternatively, a cold plant-based solvent may be been used in washing the target crystals after separation.

Embodiments are furthermore illustrated by, but not limited to the content of, the following examples.

Example 1—Production Scale 38 kg—Devolatilizing with VacOven

Slurry Making: After being warmed to 60° C., 28.3 kg of organic distillate (extracted from hemp) with a CBD concentration of 78.4% with >2% other minor cannabinoids, 9.62 kg distilled organic orange essential oil was added while the distillate stirred. The mixture continued to stir for 20 minutes. The mixture was allowed to cool to room temperature for about 5 hours and gently mixed to agitate and initiate crystallization. After 12 hours, the mixture solidified into a slushy slurry and an impeller was used to break up the clusters of crystals. This was repeated every 12 hours. After 72 hours from when the mixture was made, the slurry was ready to filter.

Filtration: A Nutsche filter was placed under vacuum (−20 PSI) then the slurry was drawn in at room temperature. The slurry was stirred with the impeller then stopped and was pressure-filtered use ultra-high purity nitrogen to collect the liquid filtrate in the source slurry container. The liquid filtrate was reintroduced into the Nutsche filter via vacuum and the filtrate was collected again, leaving the bed of crystals. The bed of crystals was stirred then reformed into a bed with the impeller, then the residual liquid was filtered via vacuum followed by a flush of pressurized nitrogen up to +15 PSI. The pressure was released then a vacuum was reapplied 10-20 PSI below atmospheric pressure.

The bed of crystals was washed with a total of 4.43 kg of cold distilled organic orange essential oils (5° C.) by drawing the liquid into the filter vessel while the crystals stirred. The bed was reformed with the impeller, vacuum- and pressure-filtered three times, as above. This washing cycle was completed 4 more times and the crystals were then harvested, yielding 7.79 kg of colorless crystals.

Devolatilization via Vacuum Oven: The harvested crystals were placed in trays containing 700 g with a calculated depth of 0.5 inch of melted oil, then placed in the vacuum oven. The oven was heated to 110° C. and vacuum reduced to <100 mTorr. The terpenes condensed on the non-heated glass door of the oven. Periodically in the first 12 hours, the vacuum was closed off from the oven and released to wipe off the volatile liquids from the glass. After 24 hours, a sample was drawn with a syringe that crystallize and ground to test for terpenes. Some were detected and so the batch continued in the vacuum oven for another 24 hours, after which no terpenes were detected.

The trays were removed and cooled at room temperature, agitated, and let set overnight. All the trays crystallized and weighed roughly 600 g. The solids were then ground into a powder and sieved to remove any larger pieces. A total of 5.28 kg was recovered with a potency of >95% CBD with non-detectable amounts of other cannabinoids.

Example 2—Production Scale 20 kg—Devolatilization Via Distillation

From a similar flow as Example 1, this example used a wipe film distillation apparatus rather than a vacuum oven to remove the residual plant-based solvents from the filtered solids. The harvest crystals which had a mass of 8.84 kg were melted to 75° C. and distilled. To remove the terpenes, the pressure of the distillation vessel was controlled between 10-15 Torr and the temperature was set for 90° C. After 3 passes, the oil was thick with no solvent was detected. The pressure was reduced to <100 mTorr and the temperature increased to 170° C. A total of 5.41 kg was recovered with a potency of >95% CBD. This was then put on tray and crystallized overnight to be ground in the morning.

Example 3—Distillation to Recover OEO and CBD from Mother Liquor

A filtrate (mother liquor) from previous filtrations were distillated to recover organic orange essential oils and CBD oil in this example. Starting with 31.66 kg mother liquor, the wipe film distillation parameters were set to 10-15 Torr and the temperature at 90° C., yielding 7.36 kg clear and colorless plant-based solvent that was reused in future crystallizations.

The distillation continued with distillation the high CBD oil with pressures <100 mTorr and temperatures at 185° C. This yielded 16.93 kg high CBD distillate to be used in future crystallizations. The overlapping fraction containing cannabinoids and essential oils was redistilled in a future distillation.

Example 4—Production Scale—Using Recovered CBD

Similar to example 3, 42.78 kg of warm organic CBD oil recovered from mother liquor and combined with 9.06 kg distill organic orange essential oils. Cooled, crystallized, filtered, and washed five times yielding 12.45 kg. The residual volatile compounds of the harvested crystals were then removed using the vacuum oven and ground to a powder similar to the example above. This yielded 10.44 kg of CBD isolate testing >95% CBD and non-detectable amounts of other cannabinoids.

Example 5—Compliant Isolate/Partial Wash with CBD Extract—Devolatilizing with Vacuum Oven A warm (55 C) 2.00 kg of organic non-winterized, concentrated $CO_2$ CBD extract with minor cannabinoids was dissolved in 0.25 kg undistilled orange essential oils. The homogenous mixture was left to crystallize over 2 days then filtered, as above. The crystal bed was washed 4 times with a total of 0.20 kg distilled orange essential oils yielding off white to yellow crystals. The volatiles from the harvested crystals were removed via vacuum oven after 1 day. The oil cooled slightly (55° C.) then poured into a container for storage, yielding 0.52 kg high CBD oil (>85%) with less than 0.3% THC. This oil later solidified and a portion was powderized.

Example 6—Small Scale with CBG Distillate—Devolatilizing with Vac-Oven

Starting with 0.92 kg distilled CBG $CO_2$ extract warmed to 60° C., 0.52 kg distilled organic essential oils was added while stirring. The mixture cooled to room temperature and was stirred daily over 1 week until the batch was filtered. The crystals were washed three times with a total of 0.23 kg of distilled orange essential oils. The crystals (0.35 kg) were devolatilized in a vacuum oven at <100 mTorr and 110° C. over 24 hours, similar to the example above, yielding 0.30 kg CBG isolate >85% CBG with no detectable amounts of other cannabinoids.

Example 7—Purity of Isolated Crystals

The following tables show cannabinoid profiles for organic crystals isolated from a crude source material, hemp.

TABLE 1

| ISOD-O-00015 Cannabidiol Isolate | |
|---|---|
| CANNABINOID PROFILE | |
| Total Cannabinoids* | 98.46% |
| CBD | 98.23% |
| CBDa | 0.00% |

TABLE 1-continued

ISOD-O-00015 Cannabidiol Isolate

| | | |
|---|---|---|
| delta 9 THC | 0.00% | |
| THCa | 0.00% | |

| Compound | LOQ (%) | Result (%) | Result (mg/g) |
|---|---|---|---|
| Delta 9-Tetrahydrocannabinolic acid (THCA-A) | 0.15 | ND | ND |
| Delta 9-Tetrahydrocannabinol (Delta 9 THC) | 0.17 | ND | ND |
| Cannabidiolic acid (CBDA) | 0.12 | ND | ND |
| Cannabidiol (CBD) | 0.12 | 98.23 | 982.3 |
| Delta 8-Tetrahydrocannabinol (Delta 8 THC) | 0.18 | ND | ND |
| Cannabinolic Acid (CBNA) | 0.11 | ND | ND |
| Cannabinol (CBN) | 0.05 | ND | ND |
| Cannabigerolic acid (CBGA) | 0.15 | ND | ND |
| Cannabigerol (CBG) | 0.04 | ND | ND |
| Tetrahydrocannabivarinic Acid (THCVA) | 0.13 | ND | ND |
| Tetrahydrocannabivarin (THCV) | 0.03 | ND | ND |
| Cannabidivarinic Acid (CBDVA) | 0.05 | ND | ND |
| Cannabidivarin (CBDV) | 0.03 | 0.14 | 1.4 |
| Cannabichromenic Acid (CBCA) | 0.06 | ND | ND |
| Cannabichromene (CBC) | 0.06 | 0.09 | 0.9 |
| Total Cannabinoids | | 98.46 | 984.6 |
| Total Potential THC** | | ND | ND |
| Total Potential CBD** | | 98.23 | 982.3 |

% = % (w/w) = Percent (Weight of Analyte/Weight of Product)
*Total Cannabinoids result reflects the absolute sum of all cannabinoids detected.
**Total Potential THC/CBD is calculated using the following formulas to take into account the loss of a carboxyl group during decarboxylation step.
Total THC = THC + (THCa * (0.877)) and Total CBD = CBD + (CBDa * (0.877))
ND = None Detected (Defined by Dynamic Range of the method)

TABLE 2

ISOG-O-00002 Cannabigerol Isolate

CANNABINOID PROFILE

| | |
|---|---|
| Total Cannabinoids* | 86.26% |
| CBD | 0.00% |
| CBDa | 0.00% |
| delta 9 THC | 0.00% |
| THCa | 0.00% |

| Compound | LOQ (%) | Result (%) | Result (mg/g) |
|---|---|---|---|
| Delta 9-Tetrahydrocannabinolic acid (THCA-A) | 0.37 | ND | ND |
| Delta 9-Tetrahydrocannabinol (Delta 9 THC) | 0.42 | ND | ND |
| Cannabidiolic acid (CBDA) | 0.48 | ND | ND |
| Cannabidiol (CBD) | 0.46 | ND | ND |
| Delta 8-Tetrahydrocannabinol (Delta 8 THC) | 0.46 | ND | ND |
| Cannabinolic Acid (CBNA) | 0.26 | ND | ND |
| Cannabinol (CBN) | 0.12 | ND | ND |
| Cannabigerolic acid (CBGA) | 0.39 | ND | ND |
| Cannabigerol (CBG) | 0.09 | 86.26 | 862.6 |
| Tetrahydrocannabivarinic Acid (THCVA) | 0.33 | ND | ND |
| Tetrahydrocannabivarin (THCV) | 0.08 | ND | ND |
| Cannabidivarinic Acid (CBDVA) | 0.20 | ND | ND |
| Cannabidivarin (CBDV) | 0.11 | ND | ND |
| Cannabichromenic Acid (CBCA) | 0.15 | ND | ND |
| Cannabichromene (CBC) | 0.16 | ND | ND |
| Total Cannabinoids | | 86.26 | 862.6 |
| Total Potential THC** | | ND | ND |
| Total Potential CBD** | | ND | ND |

% = % (w/w) = Percent (Weight of Analyte/Weight of Product)
*Total Cannabinoids result reflects the absolute sum of all cannabinoids detected.
**Total Potential THC/CBD is calculated using the following formulas to take into account the loss of a carboxyl group during decarboxylation step.
Total THC = THC + (THCa * (0.877)) and Total CBD = CBD + (CBDa * (0.877))
ND = None Detected (Defined by Dynamic Range of the method)

TABLE 3

Compliant Distillate Cannabidiol Compliant Isolate

CANNABINOID PROFILE

| | |
|---|---|
| Total Cannabinoids* | 96.79% |
| CBD | 95.99% |
| CBDa | 0.00% |
| delta 9 THC | 0.29% |
| THCa | 0.00% |

| Compound | LOQ (%) | Result (%) | Result (mg/g) |
|---|---|---|---|
| Delta 9-Tetrahydrocannabinolic acid (THCA-A) | 0.15 | ND | ND |
| Delta 9-Tetrahydrocannabinol (Delta 9 THC) | 0.17 | 0.29 | 2.9 |
| Cannabidiolic acid (CBDA) | 0.12 | ND | ND |
| Cannabidiol (CBD) | 0.11 | 95.99 | 959.9 |
| Delta 8-Tetrahydrocannabinol (Delta 8 THC) | 0.18 | ND | ND |
| Cannabinolic Acid (CBNA) | 0.10 | ND | ND |
| Cannabinol (CBN) | 0.05 | ND | ND |
| Cannabigerolic acid (CBGA) | 0.15 | ND | ND |
| Cannabigerol (CBG) | 0.04 | ND | ND |
| Tetrahydrocannabivarinic Acid (THCVA) | 0.13 | ND | ND |
| Tetrahydrocannabivarin (THCV) | 0.03 | ND | ND |
| Cannabidivarinic Acid (CBDVA) | 0.05 | ND | ND |
| Cannabidivarin (CBDV) | 0.03 | 0.19 | 1.9 |
| Cannabichromenic Acid (CBCA) | 0.06 | ND | ND |
| Cannabichromene (CBC) | 0.06 | 0.32 | 3.2 |
| Total Cannabinoids | | 96.79 | 967.9 |
| Total Potential THC** | | 0.29 | 2.9 |
| Total Potential CBD** | | 95.99 | 959.9 |

% = % (w/w) = Percent (Weight of Analyte/Weight of Product)
*Total Cannabinoids result reflects the absolute sum of all cannabinoids detected.
**Total Potential THC/CBD is calculated using the following formulas to take into account the loss of a carboxyl group during decarboxylation step.
Total THC = THC + (THCa * (0.877)) and Total CBD = CBD + (CBDa * (0.877))
ND = None Detected (Defined by Dynamic Range of the method)

TABLE 4

LD-O-00189 Recovered Cannabidiol Distillate from Mother Liquor

CANNABINOID PROFILE

| | |
|---|---|
| Total Cannabinoids* | 89.2% |
| CBD | 82.73% |
| CBDa | 0.00% |
| delta 9 THC | 1.92% |
| THCa | 0.00% |

| Compound | LOQ (%) | Result (%) | Result (mg/g) |
|---|---|---|---|
| Delta 9-Tetrahydrocannabinolic acid (THCA-A) | 0.11 | ND | ND |
| Delta 9-Tetrahydrocannabinol (Delta 9 THC) | 0.12 | 1.92 | 1.92 |
| Cannabidiolic acid (CBDA) | 0.15 | ND | ND |
| Cannabidiol (CBD) | 0.15 | 82.73 | 827.3 |
| Delta 8-Tetrahydrocannabinol (Delta 8 THC) | 0.14 | 0.18 | 1.8 |
| Cannabinolic Acid (CBNA) | 0.08 | ND | ND |
| Cannabinol (CBN) | 0.04 | 0.11 | 1.1 |
| Cannabigerolic acid (CBGA) | 0.11 | ND | ND |
| Cannabigerol (CBG) | 0.03 | 0.90 | 9.0 |
| Tetrahydrocannabivarinic Acid (THCVA) | 0.10 | ND | ND |
| Tetrahydrocannabivarin (THCV) | 0.02 | ND | ND |
| Cannabidivarinic Acid (CBDVA) | 0.06 | ND | ND |
| Cannabidivarin (CBDV) | 0.04 | 0.25 | 2.5 |

TABLE 4-continued

| LD-O-00189 Recovered Cannabidiol Distillate from Mother Liquor | | | |
|---|---|---|---|
| Cannabichromenic Acid (CBCA) | 0.04 | ND | ND |
| Cannabichromene (CBC) | 0.05 | 3.11 | 31.1 |
| Total Cannabinoids | | 89.2 | 892.0 |
| Total Potential THC** | | 1.92 | 19.2 |
| Total Potential CBD** | | 82.73 | 827.3 |

% = % (w/w) = Percent (Weight of Analyte/Weight of Product)
*Total Cannabinoids result reflects the absolute sum of all cannabinoids detected.
**Total Potential THC/CBD is calculated using the following formulas to take into account the loss of a carboxyl group during decarboxylation step.
Total THC = THC + (THCa * (0.877)) and Total CBD = CBD + (CBDa * (0.877))
ND = None Detected (Defined by Dynamic Range of the method)

As can be easily understood from the foregoing, the basic concepts of the various embodiments of the present invention(s) may be embodied in a variety of ways. It involves both isolating techniques as well as devices to accomplish the appropriate isolate. In this application, the isolating techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the various embodiments of the invention(s) and may not explicitly show how each feature or element can actually be representative of a broader function or of a great variety of alternative or equivalent elements. As one example, terms of degree, terms of approximation, and/or relative terms may be used. These may include terms such as the words: substantially, about, only, and the like. These words and types of words are to be understood in a dictionary sense as terms that encompass an ample or considerable amount, quantity, size, etc. as well as terms that encompass largely but not wholly that which is specified. Further, for this application if or when used, terms of degree, terms of approximation, and/or relative terms should be understood as also encompassing more precise and even quantitative values that include various levels of precision and the possibility of claims that address a number of quantitative options and alternatives. For example, to the extent ultimately used, the existence or non-existence of a substance or condition in a particular input, output, or at a particular stage can be specified as substantially only x or substantially free of x, as a value of about x, or such other similar language. Using percentage values as one example, these types of terms should be understood as encompassing the options of percentage values that include 99.5%, 99%, 97%, 95%, 92% or even 90% of the specified value or relative condition; correspondingly for values at the other end of the spectrum (e.g., substantially free of x, these should be understood as encompassing the options of percentage values that include not more than 0.5%, 1%, 3%, 5%, 8% or even 10% of the specified value or relative condition, all whether by volume or by weight as either may be specified). In context, these should be understood by a person of ordinary skill as being disclosed and included whether in an absolute value sense or in valuing one set of or substance as compared to the value of a second set of or substance. Again, these are implicitly included in this disclosure and should (and, it is believed, would) be understood to a person of ordinary skill in this field. Where the application is described in device-oriented terminology, each element of the device implicitly performs a function. Apparatus claims may not only be included for the device described, but also method or process claims may be included to address the functions of the embodiments and that each element performs. Neither the description nor the terminology is intended to limit the scope of the claims that will be included in any subsequent patent application.

It should also be understood that a variety of changes may be made without departing from the essence of the various embodiments of the invention(s). Such changes are also implicitly included in the description. They still fall within the scope of the various embodiments of the invention(s). A broad disclosure encompassing the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of embodiments of the invention(s) both independently and as an overall system.

Further, each of the various elements of the embodiments of the invention(s) and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the various embodiments of the invention(s), the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which embodiments of the invention(s) is entitled. As but one example, it should be understood that all actions may be expressed as a means for taking that action or as an element which causes that action. Similarly, each physical element disclosed should be understood to encompass a disclosure of the action which that physical element facilitates.

Regarding this last aspect, as but one example, the disclosure of a "mixer" should be understood to encompass disclosure of the act of "mixing"—whether explicitly discussed or not—and, conversely, were there effectively disclosure of the act of "mixing", such a disclosure should be understood to encompass disclosure of a "mixer" and even a "means for mixing." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function. As other non-limiting examples, it should be understood that claim elements can also be expressed as any of: components, programming, subroutines, logic, or elements that are configured to, or configured and arranged to, provide or even achieve a particular result, use, purpose, situation, function, or operation, or as components that are capable of achieving a particular activity, result, use, purpose, situation, function, or operation. All should be understood as within the scope of this disclosure and written description.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the information statement filed with the application are hereby appended and hereby incorporated by reference, however, as to each of the above, to the extent that such information or statements incorporated by reference might be considered inconsistent with the patenting of the various embodiments of invention(s) such statements are expressly not to be considered as made by the applicant(s).

Thus, the applicant(s) should be understood to have support to claim and make claims to embodiments including at least: i) each of the isolation devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such processes, methods, systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC*, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrases "comprising", "including", "containing", "characterized by" and "having" are used to maintain the "open-end" claims herein, according to traditional claim interpretation including that discussed in MPEP § 2111.03. Thus, unless the context requires otherwise, it should be understood that the terms "comprise" or variations such as "comprises" or "comprising", "include" or variations such as "includes" or "including", "contain" or variations such as "contains" and "containing", "characterized by" or variations such as "characterizing by", "have" or variations such as "has" or "having", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 9 or any other claim" or the like, it could be re-drafted as dependent on claim 1, claim 8, or even claim 11 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the various embodiments of the application, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A method for isolating compounds comprising the steps of:
   providing a crude source material having a target compound and at least one non-target compound;
   adding a non-ethanol plant-based solvent to said crude source material;
   mixing said crude source material with said non-ethanol plant-based solvent to form a solution;
   forming crystals comprising said target compound from said solution;
   separating said crystals comprising said target compound from said solution; and
   yielding organic crystals of said target compound from said crude source material.

2. The method as described in claim 1 wherein said crude source material is chosen from oil extracted from *Cannabis sativa*, and oil extracted from USDA certified organic high-cannabidiol *Cannabis sativa*.

3. The method as described in claim 1 wherein said target compound is chosen from cannabidiol, cannabigerol, cannabinol, cannabidiolic acid, cannabigerolic acid, cannabichromene, cannabidivarin, vitamins, nutraceuticals, supplements, pharmaceuticals, phtyochemicals, and cannabinoids excluding tetrahydrocannabinol.

4. The method as described in claim 1 wherein said non-ethanol plant-based solvent is chosen from essential oils, terpenes, terpenoids, nut oils, cooking oils, and any combination thereof.

5. The method as described in claim 1 wherein said non-ethanol plant-based solvent comprises an essential oil.

6. The method as described in claim 5 wherein said essential oil comprises orange essential oil.

7. The method as described in claim 1 wherein said at least one non-target compound is chosen from solvents, residual solvents, ethanol, terpenes, waxes, cannabinoids, tetrahydrocannabinol, tetrahydrocannabinolic acid, mycotoxins, herbicides, pesticides, heavy metals, agrochemicals, phytochemicals, lipids, and any combination thereof.

8. The method as described in claim 1 and further comprising a step of containing said crude source material in a vessel.

9. The method as described in claim 8 wherein said vessel is chosen from a temperature-controlled vessel, a stainless-steel vessel, a jacketed vessel, a high-density polyethylene vessel, a food grade plastic vessel, a glass vessel, and any combination thereof.

10. The method as described in claim 1 and further comprising a step of cooling said solution.

11. The method as described in claim 10 wherein said step of cooling said solution comprises a step of cooling said solution to a temperature between about 20° C. and about 2° C.

12. The method as described in claim 1 wherein said step of forming crystals comprising said target compound from said solution comprises a step of breaking up said crystals.

13. The method as described in claim 1 and further comprising a step of filtering said solution before said step of forming crystals.

14. The method as described in claim 1 and further comprising a step of providing a ratio of non-ethanol plant-based solvent to crude source material of between about 2% non-ethanol plant-based solvent to about 98% crude source material to about 75% non-ethanol plant-based solvent to about 25% crude source material.

15. The method as described in claim 1 and further comprising a step of inducing crystallization in said solution with a step chosen from:
   adding a single crystal comprising said target compound to said solution;
   adding up to about 10% of total mass of said target compound to said solution;
   providing a container containing said solution with a rough surface; and
   stirring said solution.

16. The method as described in claim 1 wherein said step of separating said crystals from said solution comprises a step chosen from:
   filtering said crystals from said solution;
   vacuum filtering said crystals from said solution;
   pressure filtering said crystals with gas from said solution; and
   pressure filtering said crystals with nitrogen gas from said solution.

17. The method as described in claim 1 and further comprising a step of, after said step of separating said crystals from said solution, collecting a residual composite comprising a remaining part of said solution.

18. The method as described in claim 17 and further comprising the steps of:
   cooling said residual composite at a lower temperature than a temperature of said solution;
   forming supplementary crystals comprising said target compound from said residual composite; and
   collecting said supplementary crystals.

19. The method as described in claim 17 wherein said residual composite comprises a filtrate.

20. The method as described in claim 1 and further comprising a step of washing said crystals with a wash solution after said crystals have been separated from said solution.

21. The method as described in claim 20 wherein said step of washing said crystals with said wash solution after said crystals have been separated from said solution comprises a step of rewashing said crystals with said wash solution.

22. The method as described in claim 20 wherein said wash solution is chosen from a residual composite, said non-ethanol plant-based solvent, a different non-ethanol plant-based solvent, a solvent mixed with said target compound, a solvent mixed with said crude source material, and any combination thereof.

23. The method as described in claim 20 and further comprising a step of cooling said wash solution before using to wash said crystals.

24. The method as described in claim 20 and further comprising a step of removing said wash solution from said crystals after said step of washing said crystals.

25. The method as described in claim 24 wherein said step of removing said wash solution from said crystals comprises a step chosen from:
removing said wash solution from said crystals with high pressure gas;
removing said wash solution from said crystals with liquid;
removing said wash solution from said crystals with a supercritical fluid;
removing said wash solution from said crystals with distillation;
removing said wash solution from said crystals with vacuum filtration;
removing said wash solution from said crystals with vacuum filtration while using a blanket of inert gas during said filtration;
adding heat to said crystals;
adding heat to said crystals while pulling a deep vacuum;
heating said crystals in a vacuum oven; and
processing said crystals in a distillation apparatus.

26. The method as described in claim 1 and further comprising a step of turning said organic crystals into free-flowing powder.

27. The method as described in claim 1 wherein said step of yielding organic crystals of said target compound from said crude source material is done without using a centrifuge.

28. The method as described in claim 17 and further comprising a step of separating said non-ethanol plant-based solvent in said residual composite and reusing in said method.

29. The method as described in claim 1 wherein said organic crystals of said target compound comprises organic cannabidiol having a purity of greater than about 95%.

30. A system to isolate compounds comprising:
a vessel configured to contain a crude source material having a target compound and at least one non-target compound;
a non-ethanol plant-based solvent configured to be added to said crude source material in said vessel;
a mixer configured to mix said crude source material with said non-ethanol plant-based solvent to form a solution;
a crystal separator configured to separate crystals comprising said target compound from said solution; and
a collection of organic crystals of said target compound isolated from said crude source material.

31. The method as described in claim 1 and further comprising a step of pre-processing said non-ethanol plant-based solvent.

32. The method as described in claim 31 wherein said step of pre-processing said non-ethanol plant-based solvent comprises a step of treating said non-ethanol plant-based solvent to remove at least one impurity.

33. The method as described in claim 32 wherein said impurity comprises color.

34. The method as described in claim 8 and further comprising a step of adding said crude source material to a warm vessel that is greater than about 20° C.

35. The method as described in claim 1 and further comprising a step of warming said crude source material to a temperature greater than about 40° C.

36. The method as described in claim 35 and further comprising the steps of:
warming said non-ethanol plant-based solvent when added to said warm crude source material; and
warming said solution while mixing said crude source material with said non-ethanol plant-based solvent.

37. The method as described in claim 1 and further comprising a step of determining when crystallization of said solution is complete before said step of separating said crystals from said solution.

38. The method as described in claim 37 wherein said step of determining when crystallization of said solution is complete comprises a step chosen from:
monitoring a temperature of said solution;
monitoring said target compound concentration in said solution;
monitoring an amount of time said solution has been cooled; and
monitoring an appearance of said solution.

39. The method as described in claim 23 wherein said step of cooling said wash solution before using to wash said crystals comprises a step of cooling said wash solution to between about −40° C. and about 40° C. before using to wash said crystals.

40. The method as described in claim 24 and further comprising a step of clarifying said crystals after said step of removing said wash solution.

41. The method as described in claim 40 wherein said step of clarifying said crystals comprise a step chosen from:
mixing said crystals with activated charcoal;
mixing said crystals with bentonite clay; and
mixing said crystals with silica gel.

42. The method as described in claim 17 and further comprising a step of separating said target compound in said residual composite.

43. The system as described in claim 30 wherein said crude source material is chosen from oil extracted from *Cannabis sativa*, and oil extracted from USDA certified organic high-cannabidiol *Cannabis sativa*.

44. The system as described in claim 30 wherein said target compound is chosen from cannabidiol, cannabigerol, cannabinol, cannabidiolic acid, cannabigerolic acid, cannabichromene, cannabidivarin, vitamins, nutraceuticals, supplements, pharmaceuticals, phtyochemicals, and cannabinoids excluding tetrahydrocannabinol.

45. The system as described in claim 30 wherein said non-ethanol plant-based solvent is chosen from essential oils, terpenes, terpenoids, nut oils, cooking oils, and any combination thereof.

46. The system as described in claim 30 wherein said non-ethanol plant-based solvent comprises an essential oil.

47. The system as described in claim 46 wherein said essential oil comprises orange essential oil.

48. The system as described in claim 30 wherein said at least one non-target compound is chosen from solvents, residual solvents, ethanol, terpenes, waxes, cannabinoids, tetrahydrocannabinol, tetrahydrocannabinolic acid, mycotoxins, herbicides, pesticides, heavy metals, agrochemicals, phytochemicals, lipids, and any combination thereof.

49. The system as described in claim 30 wherein said vessel is chosen from a temperature-controlled vessel, a stainless-steel vessel, a jacketed vessel, a high-density polyethylene vessel, a food grade plastic vessel, a glass vessel, and any combination thereof.

50. The system as described in claim 30 and further comprising a cooler configured to cool said solution.

51. The system as described in claim 50 wherein said cooler is configured to cool said solution to a temperature of around 20° C.

52. The system as described in claim 30 and further comprising a crystal breaker configured to break said crystals.

53. The system as described in claim 30 wherein said crystal separator is chosen from a filter, vacuum filter, pressure filter, pressure filter with gas, and pressure filter with nitrogen gas.

54. The system as described in claim 30 and further comprising wash solution configured to wash said crystals after said crystals have been separated from said solution.

55. The system as described in claim 54 wherein said wash solution is chosen from said residual composite, said non-ethanol plant-based solvent, a different non-ethanol plant-based solvent, a solvent mixed with said target compound, a solvent mixed with said crude source material, and any combination thereof.

56. The system as described in claim 30 wherein said collection of said organic crystals of said target compound comprises organic cannabidiol having a purity of greater than about 95%.

* * * * *